United States Patent
Fredriksson

(10) Patent No.: US 11,224,762 B2
(45) Date of Patent: Jan. 18, 2022

(54) SYSTEM AND METHOD FOR AUTOMATIC RADIOTHERAPY TREATMENT PLANNING

(71) Applicant: RaySearch Laboratories AB, Stockholm (SE)

(72) Inventor: Albin Fredriksson, Stockholm (SE)

(73) Assignee: RaySearch Laboratories AB, Stockholm (SE)

(*) Notice: Subject to any disclaimer, the term of this patent is extended or adjusted under 35 U.S.C. 154(b) by 253 days.

(21) Appl. No.: 16/500,204

(22) PCT Filed: Apr. 4, 2018

(86) PCT No.: PCT/EP2018/058581
§ 371 (c)(1),
(2) Date: Oct. 2, 2019

(87) PCT Pub. No.: WO2018/185146
PCT Pub. Date: Oct. 11, 2018

(65) Prior Publication Data
US 2021/0101021 A1    Apr. 8, 2021

(30) Foreign Application Priority Data
Apr. 5, 2017  (EP) .................................. 17165042

(51) Int. Cl.
*A61N 5/10*    (2006.01)

(52) U.S. Cl.
CPC ......... *A61N 5/1031* (2013.01); *A61N 5/1038* (2013.01); *A61N 2005/1041* (2013.01)

(58) Field of Classification Search
None
See application file for complete search history.

(56) References Cited

U.S. PATENT DOCUMENTS

| | | | |
|---|---|---|---|
| 2011/0191085 A1* | 8/2011 | Jaffray | G06G 7/60 703/11 |
| 2015/0141733 A1 | 5/2015 | Kumar et al. | |
| 2016/0303398 A1 | 10/2016 | Eriksson | |

FOREIGN PATENT DOCUMENTS

| WO | WO-2014/197994 A1 | 12/2014 |
|---|---|---|
| WO | WO-2015/083035 A1 | 6/2015 |

* cited by examiner

*Primary Examiner* — Hoon K Song
(74) *Attorney, Agent, or Firm* — Faegre Drinker Biddle & Reath LLP

(57) ABSTRACT

A method of radiotherapy treatment planning comprises optimizing a treatment plan based on at least one proposed dose map according to a set of clinical goals The resulting dose distribution is compared to the at least one clinical goal, and if the optimized dose distribution does not fulfil the at least one clinical goal, continuing with step d the dose map is adjusted before a new treatment plan is optimized. When the optimized dose distribution fulfils the clinical goals, the treatment plan is accepted.

11 Claims, 1 Drawing Sheet

SYSTEM AND METHOD FOR AUTOMATIC RADIOTHERAPY TREATMENT PLANNING

This application is the National Stage of International Application No. PCT/EP2018/058581, filed Apr. 4, 2018, and claims benefit of European Patent Application No. 17165042, filed Apr. 5, 2017, the entire contents of which are incorporated by reference herein.

TECHNICAL FIELD

The present invention relates to a system, a method and a computer program product for radiotherapy treatment planning, and in particular for contributing to the automation of such planning.

BACKGROUND

In radiotherapy, the goal is typically to deliver a sufficiently high radiation dose to a target (for example a tumour) within the patient, while sparing surrounding normal tissue as much as possible. In particular, it is important to minimize the dose to sensitive organs close to the target. A treatment plan defining treatment parameters, such as treatment machine settings, to be used in a radiotherapy treatment session, is usually determined with the aid of a computer-based treatment planning system.

In inverse treatment planning, an optimization algorithm is employed for finding a set of treatment parameters that will generate an acceptable dose distribution within the subject, preferably satisfying all the clinical goals defined by the clinician. Clinical goals can take many forms. Some of the common ones include

- requirements that a specified minimum or maximum dose should be delivered to at least or at most a specified fraction or volume of a Region of Interest (ROI),
- requirements that a specified minimum or maximum fraction or volume of an ROI should receive at least or at most a specified dose,
- requirements on the minimum, maximum, or average dose to an ROI, requirements on how well the dose conforms to the target,
- requirements on the homogeneity in the target,
- requirements on how the dose falls off with the distance to the target,
- requirements that a certain point in the patient should receive a specified dose, and
- requirements on biological measures such as the tumour control probability or normal tissue complication probability in an ROI.

Traditionally, a lot of manual input is required in treatment plan optimization. The result in general depends on the experience of the treatment planner and, for example, the selection of treatment objectives used for the optimization. Still, the process does not in any way guarantee that the best possible treatment plan is obtained. A substantial amount of "trial-and-error" is usually required, even for an experienced treatment planner, before an acceptable treatment plan has been found. Furthermore, if a dose distribution of an optimized treatment plan is satisfactory in most regards but comprises some small deficiency, it might not be apparent to a treatment planner how to adjust the optimization objectives or constraints, or the objective weights, in order to remedy the deficiency. Automating the optimization process has proven to be difficult since the current methods are based to a great extent on human judgement which is difficult to automate.

An aim of the present invention is to overcome, or at least mitigate, the drawbacks described above, and in particular to facilitate automatic treatment planning with optimal fulfilment of clinical goals.

SUMMARY

The invention relates to a method of computer-based radiotherapy treatment planning, comprising
a. obtaining at least one proposed dose map to be used in treatment planning for a patient, said at least one dose map specifying at least one desired dose level for at least a first region of the patient in accordance with a set of clinical goals comprising at least one clinical goal for the patient,
b. optimizing a treatment plan based on the dose map, to obtain an optimized dose distribution,
c. comparing the optimized dose distribution of the treatment plan to the at least one clinical goal, and if the optimized dose distribution does not fulfil the at least one clinical goal, continuing with step d.
d. based on the result of the comparison, adjusting the at least one dose map in at least one region where the optimized dose distribution does not meet the at least one clinical goal,
e. repeating steps b. to d. for the at least one adjusted dose map, When it is determined in step c. that the optimized dose distribution fulfils the at least one clinical goal, the procedure stops. This normally involves accepting the treatment plan, which may then be used for patient treatment.

Hence, the proposed method is based on attempting to mimic a proposed dose map, by optimizing a plan with the aim of producing a dose distribution corresponding to the dose map. The dose map is iteratively updated on the basis of how well the plan optimized to mimic the dose map satisfies the clinical goals. According to the invention, this may be done in a completely automated manner. In particular, the steps c. and d. are preferably performed in a computer, without the need for user input.

An optimization is performed which, at least in part, aims at obtaining a specific dose distribution, which has been specified with the purpose of fulfilling the clinical goals. Such optimization is herein referred to as "dose mimicking", indicating that the goal of the optimization is to find a set of treatment parameters which produces a dose distribution which as closely as possible matches or "mimics" a specific desired dose distribution, which is called dose map. Dose mimicking could be based on a spatial dose map, i.e. using reference dose objectives which are different and specific for each voxel. The optimization then aims, at least partly, to achieve a dose distribution in which each voxel is as similar as possible to, or as little above/below as possible, the dose levels specified in the spatial dose map. Alternatively, or additionally, dose mimicking could be based on a dose map corresponding to specific dose volume histograms (DVHs), i.e. using the previously obtained DVH curves as references in the optimization. In this case, the optimization aims to achieve a dose distribution in a given ROI that need not be spatially as close as possible to a spatial dose map, but the DVH of which is as similar as possible to, or as little above/below as possible, the DVH of a dose map.

Mimicking may also relate to more than one dose map. The dose map or dose maps are preferably obtained on the basis of one or more of the following:

a. the dose and volume levels of the clinical goals
b. a previously created manual plan for the current or another patient
c. knowledge-based prediction The method preferably comprises the step of determining a direction and a magnitude for at least one adjustment of the dose map, said direction and magnitude being determined with the aim of achieving a resulting dose distribution closer to fulfilling the clinical goals.

Adjustment of the dose map may be performed by setting at least one new dose value for at least one voxel. Alternatively, adjustment of the dose map is performed by setting at least one new importance weight for at least one voxel. Yet another option is to adjust the dose map by adjusting target DVH curves for at least one volume within the patient.

The step of adjusting the dose map, based on the result of the comparison, in at least one region where the optimized dose distribution does not meet the at least one clinical goal preferably comprises determining at least one voxel where the calculated optimized dose deviates from at least one clinical goal for a region at least partly comprising that voxel, determining the direction of the deviation and adjusting the dose map in that voxel to force the dose for the at least one voxel closer to at least one clinical goal for a region at least partly comprising the at least one voxel.

The set of clinical goals preferably comprises at least two clinical goals for the patient. The clinical goals may be prioritized into at least two priority levels, in which case the adjustment of the dose map may be determined based on the priority levels of the clinical goals. The adjustment of the dose map may then be determined in accordance with the clinical goal having the highest priority. Alternatively, the adjustment of the dose map may be determined in accordance with more than one goal, for example as a weighted mean between the goals. If there are goals associated with non-overlapping regions, or goals for the same region favour adjustments in the same direction, the adjustment of the dose map may be determined in accordance with multiple goals.

The invention also relates to a computer program product comprising computer readable code means which, when run in a processor, will cause the processor to perform the method according to any one of the preceding claims. The computer program product may be stored on a memory unit, such as a non-transitory memory unit. Further, the invention relates to a computer system comprising a processor and a program memory, such as a non-transitory program memory, holding a computer program product according to the above.

The invention also relates to a treatment planning system comprising a processor, at least one data memory comprising data for obtaining a treatment plan, including a set of clinical goals and at least one dose map to be used for the planning, and at least one program memory comprising a computer program product according to the above.

BRIEF DESCRIPTION OF THE DRAWINGS

The invention will be described in more detail in the following, by way of example and with reference to the appended drawings, in which.

DETAILED DESCRIPTION

Figure 1:
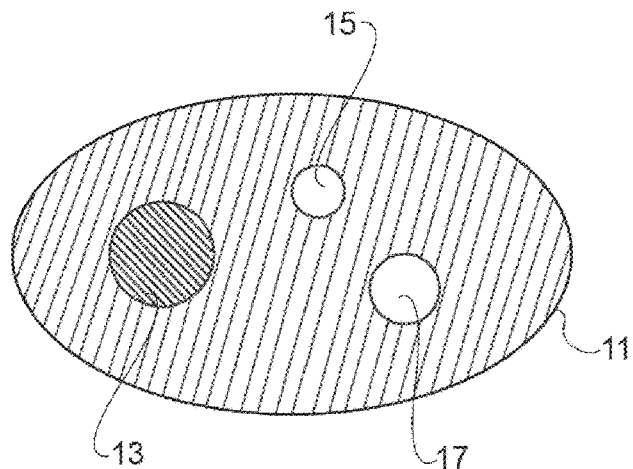
FIG. 1 is a schematic illustration of a dose map.

FIG. 1 is a schematic illustration of a dose map in a section 11 through a patient. A first region 13 corresponds to a target and the dark colouring reflects that this region should receive a high dose. Two regions 15, 17, which should receive a low dose, typically organs at risk, are shown with no colouring. The rest of the section is lightly coloured, meaning the dose should be restricted but is not as critical as for the organs at risk 15, 17. As will be understood, any suitable number of different dose levels could be set. Also, typically, the section is divided into voxels and there will be a table or similar specifying the dose level for each voxel as a numeric value.

Figure 2:
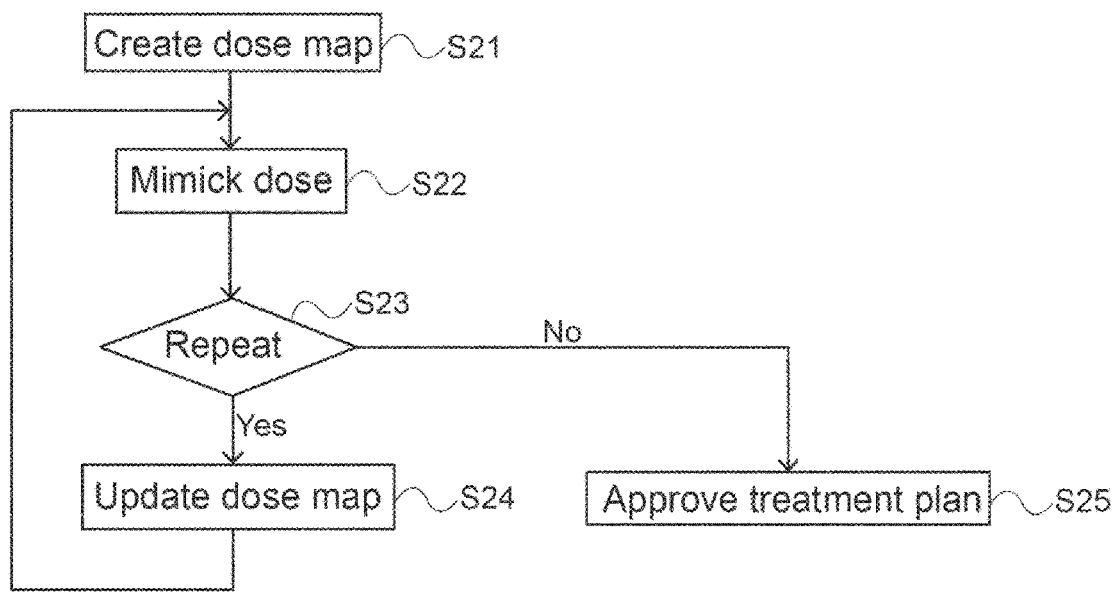
FIG. 2 is a flowchart outlining a method according to an embodiment of the invention.

FIG. 2 is a flowchart outlining a method according to an embodiment of the invention. As will be understood, the method is performed by means of one or more computer programs in a computer. In a first step S21, a proposed dose distribution for a treatment for a particular patient is generated, based on clinical goals and data about the patient. The proposed dose distribution prescribes dose values for each region of the patient and is often referred to as a dose map. This initial dose map may be calculated using any suitable method as will be discussed below. It is also possible to use more than one dose map, including two or more. For example, using one upper bound and one lower bound dose map is well known in the art.

The dose planning in step S21 may be performed in any suitable way, typically in accordance with a set of rules defining relationships between applied dosage, the treatment plan class and at least one feature of the image data, for example by means of interference techniques, which are known per se, for example from WO 2014/197994. The rules may include rules generated by machine learning, mathematical functions and other rules as will be familiar to the skilled person. The proposed dose map may define the proposed dose over a volume of the image data. For example, knowledge-based planning may be used to generate an initial dose map. Alternatively, the initial dose map may be based on clinical goals only.

The initial dose map or dose maps may be specified on a voxel-by-voxel basis. Each voxel, or other sub-region of the image, may be characterized by one or more appearance features, such as which anatomical structure it belongs to, density, or other features of the image. Then, the set of rules may be used to relate the voxel features to the treatment plan class and optionally other patient features such as age or part of the body. The clinical goals may also be used to define an isodose or DVH curves.

In step S22, a dose mimicking is performed. The term dose mimicking, used in this document, means optimizing a treatment plan, based on the dose map (or dose maps), with the aim of obtaining a dose distribution that is to be evaluated. The ultimate goal is to arrive at a dose distribution fulfilling the clinical goals, within certain limits. The optimization can be performed in a number of ways, for example, by penalizing the deviation of the dose in each voxel from the dose level of the corresponding voxel in the dose map(s), and optimizing toward finding a plan with as low penalty as possible. If an upper bound dose map is used, only deviations above its specified dose levels are penalized. Similarly, if a lower bound dose map is used, only deviations below its specified dose levels are penalized. The penalties for each voxel may have individual importance weights. In the first iteration of the loop S22-S24 the optimization is based on mimicking the initial dose map.

Step S23 is a decision step to determine whether to perform another loop in the optimization process. If the result of the dose mimicking in step S22 is not satisfactory, the answer in step S23 will be yes, and the process will continue with step S24, in which the dose map or dose maps are adjusted. Thereafter, the process returns to step S22 where dose mimicking is performed based on the adjusted dose map or dose maps. If the answer in step S23 is no, the method continues in step S25, in which the treatment plan is accepted. This means, that if the resulting dose distribution in step S22 is deemed not to fulfil the clinical goals sufficiently well, the dose map or dose maps are adjusted in such a way as to make the resulting dose distribution closer to the clinical goals. If the resulting dose distribution in step S22 is deemed to fulfil the clinical goals, no further adjustment of the dose map is needed, and the treatment plan optimized in step S22 is accepted. The treatment plan may then be used for treatment of a patient.

The adjustment of the dose map in step S24 is preferably made automatically by the computer program, to adjust the resulting dose in one or more sub-regions of the dose map. For example, if in the treatment plan resulting from step S22 a particular voxel or group of voxels receives a too high dose according to the clinical goals, the dose in these voxels in the dose map may be reduced. Similarly, if in the treatment plan resulting from step S22 a particular voxel or group of voxels receives a too low dose according to the clinical goals, the dose in these voxels in the dose map may be increased. Hence, in step S23 or S24 the voxels or regions in which the clinical goals are not fulfilled are identified and the direction and magnitude of the deviation are determined, to enable appropriate adjustment of the dose values in step S24. Hence, the adjusted dose map or dose maps output from step S24 may specify dose levels in one or more regions of the dose map or dose maps that do not correspond to actual desired dose in the region, but are intended to affect the dose in the desired direction.

The adjustment of the dose map may be performed by setting new dose values individually for the voxels, or groups of voxels that are to be adjusted, or by specifying an increase or a decrease for the voxel or group of voxels. Alternatively, the adjustment may be performed by adjusting target DVH curves.

The voxels to be adjusted, and the magnitude and direction of the adjustment, can be determined in a number of different ways. For example, for a clinical goal that prescribes a minimum dose to a region, the sub-regions with doses below this level can be selected to be adjusted. The magnitude of the adjustment could be correlated to the deviation from the prescribed dose level. For a clinical goal that prescribes a minimum or maximum dose level to a certain percentage x of a region in the patient, the voxels could be ordered according to their current dose levels in the dose distribution, and the x % voxels with the highest or lowest dose, respectively, could be selected to be adjusted, or selected to be adjusted if they fail to reach the minimum or maximum dose level, respectively. Similar methods for selecting the voxels to be adjusted could be specified for average dose goals, dose fall-off goals, etc.

Determining, in step S23, whether or not the resulting dose distribution fulfils the clinical goals sufficiently well, typically involves comparing the dose distribution for at least one region of the patient to at least one clinical goal for that region. If the dose distribution does not deviate by more than a specified amount, or percentage, from the at least one clinical goal, the dose distribution is considered to fulfil that at least one goal. Similarly, if the dose distribution deviates more than the specified amount, or percentage, the dose distribution is not considered to fulfil the at least one goal. In some cases, the goals for one region may be met while the goals for another region are not met. In such cases it may be decided that the fulfilment of some goals is sufficient to accept the treatment plan even though other goals are not fulfilled so that the treatment plan may be accepted in step S25. Alternatively, it may be decided that the goals as a whole are not fulfilled so that the procedure should continue with step S24. Alternatively, it may be decided that the treatment plan is accepted in step S25 if computational resources such as time or number of acceptable steps taken have run out.

If there are conflicting goals for the same sub-region, the direction of the adjustment can be determined on the basis of the priority of the goals. For example, if one goal has a higher priority than another goal, the goal having the highest priority may be used to determine the adjustment. Alternatively, a compromise between the goals may be determined and used for determining the adjustment. For example, a weighted mean of their desired updates can be applied. This is particularly relevant if the goals have the same priority level.

Figure 3:
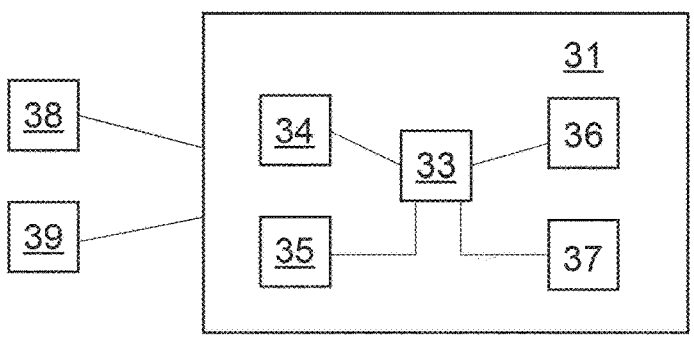
FIG. 3 is a schematic overview of a computer system in which the method according to embodiments of the invention may be implemented.

FIG. 3 is a schematic representation of a system for radiotherapy planning and treatment, in which the inventive method may be performed. A computer 31 comprises a processor 33, a first and a second data memory 34, 35 and a first and a second program memory 36, 37. Preferably, one or more user input means 38, 39 are also present, in the form of a keyboard, a mouse, a joystick, voice recognition means or any other available user input means. The user input means may also be arranged to receive data from an external memory unit.

The first data memory 34 comprises clinical data and/or other information used to obtain a treatment plan. The second data memory 35 one or more dose maps for one or more patients to be used in treatment planning according to embodiments of the invention. The first program memory 36 holds a computer program, known per se, arranged for treatment plan optimization. The second program memory 37 holds a computer program arranged to make the computer perform the method steps discussed in connection with FIG. 2.

As will be understood, the data memories 34, 35 and the program memories are shown and discussed schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

The invention claimed is:

1. A method of computer-based radiotherapy treatment planning, comprising
   a. obtaining at least one proposed dose map to be used in treatment planning for a patient, said at least one dose map specifying at least one desired dose level for at least a first region of the patient in accordance with a set of clinical goals comprising at least one clinical goal for the patient;
   b. optimizing a treatment plan based on the dose map, to obtain an optimized dose distribution;
   c. comparing the optimized dose distribution of the treatment plan to the at least one clinical goal to decide whether the optimized dose distribution fulfils the at least one clinical goal;
   d. based on the result of the comparison, responsive to deciding that the optimized dose distribution does not fulfil the at least one clinical goal, determining a penalty based on a deviation of a dose level in each voxel of the optimized dose distribution from a dose level of a corresponding voxel based on the at least one clinical goal, wherein the penalty includes at least one importance weight for at least one voxel based on the deviation, and adjusting the dose map in at least one region where the optimized dose distribution does not meet the at least one clinical goal based on the determined penalty;
e. repeating steps b. to d. for the adjusted dose map; and
f. when it is determined in step c. that the optimized dose distribution fulfils the at least one clinical goal, accepting the treatment plan.

2. The method according to claim 1, wherein the dose map is obtained on the basis of one or more of the following:
a. the dose and volume levels of the clinical goals;
b. a previously created manual plan for the current or another patient; and
c. knowledge-based prediction.

3. The method according to claim 1, comprising the step of determining a direction and a magnitude for at least one adjustment of the at least one dose map, said direction and magnitude being determined to lead to a resulting dose distribution closer to fulfilling the clinical goals.

4. The method according to claim 1, wherein adjustment of the at least one dose map is performed by setting at least one new dose value for the at least one voxel for which the penalty is determined.

5. The method according to claim 1, wherein adjustment of the dose map is performed by adjusting target DVH curves for at least one volume within the patient.

6. The method according to claim 1, wherein step d. comprises determining the direction of the deviation and adjusting the dose map in the at least one voxel for which the penalty is determined to force the dose for the at least one voxel closer to at least one clinical goal for a region at least partly comprising the at least one voxel.

7. The method according to claim 1 in which the set of clinical goals comprises at least two clinical goals for the patient, which are prioritized into at least two priority levels, and where the adjustment of the dose map is determined based on the priority levels of the clinical goals.

8. The method according to claim 7, wherein the adjustment of the dose map is determined in accordance with the clinical goal having the highest priority.

9. The method according to claim 8, wherein the adjustment of the dose map is determined in accordance with more than one goal, for example as a weighted mean between the goals.

10. A computer program product comprising computer readable code means which, when run in a processor, will cause the processor to perform the method according to claim 1.

11. The computer system comprising a processor and a program memory holding a computer program product according to claim 10.

* * * * *